(12) United States Patent
Sommermeyer et al.

(10) Patent No.: US 7,285,661 B2
(45) Date of Patent: Oct. 23, 2007

(54) STARCH DERIVATIVES, STARCH ACTIVE SUBSTANCE CONJUGATES, METHOD FOR THE PRODUCTION THEREOF AND THEIR USE AS MEDICAMENTS

(75) Inventors: Klaus Sommermeyer, Rosbach v.d.H. (DE); Norbert Zander, Meine (DE); Ronald Frank, Meine-Grassel (DE); Harald Conradt, Braunschweig (DE)

(73) Assignee: Fresenius Kabi Deutschland GmbH, Bad Homburg V.D.H. (DE)

( * ) Notice: Subject to any disclaimer, the term of this patent is extended or adjusted under 35 U.S.C. 154(b) by 544 days.

(21) Appl. No.: 10/504,892

(22) PCT Filed: Feb. 20, 2003

(86) PCT No.: PCT/EP03/01716

§ 371 (c)(1),
(2), (4) Date: Oct. 21, 2004

(87) PCT Pub. No.: WO03/070772

PCT Pub. Date: Aug. 28, 2003

(65) Prior Publication Data

US 2005/0065113 A1 Mar. 24, 2005

(30) Foreign Application Priority Data

Feb. 20, 2002 (DE) .................. 102 07 072

(51) Int. Cl.
*C08B 31/00* (2006.01)
*C08B 33/00* (2006.01)
*C08B 35/00* (2006.01)
*C07H 5/04* (2006.01)

(52) U.S. Cl. .................. 536/45; 536/53; 536/55.3

(58) Field of Classification Search .................. 536/45, 536/53, 55.3
See application file for complete search history.

(56) References Cited

U.S. PATENT DOCUMENTS 6,083,909 A 7/2000 Sommermeyer et al.

FOREIGN PATENT DOCUMENTS

| DE | 196 28 705 A1 | 1/1998 |
|---|---|---|
| DE | 101 35 694 A1 | 2/2003 |
| FR | 2 600 897 A | 1/1988 |

*Primary Examiner*—Shaojia Anna Jiang
*Assistant Examiner*—Everett White
(74) *Attorney, Agent, or Firm*—Hamilton, Brook, Smith & Reynolds, P.C.

(57) ABSTRACT

The invention relates to starch derivatives of formula (I), in which: X represents a bromine or iodine atom; R" represents a straight-chain or branched alkyl group, aryl group or aralkyl group, and; R—CO— represents an oxidized substituted or unsubstituted starch radical that is oxidized on the reducing terminal group to form a carboxylic acid. Starch derivatives of formula (I) can selectively couple to active substances containing SH groups and have a prolonged half-life period in the human body. The invention also relates to coupling products of compound (I) with active substances, to methods for the production thereof, and to their use as medicaments (I)

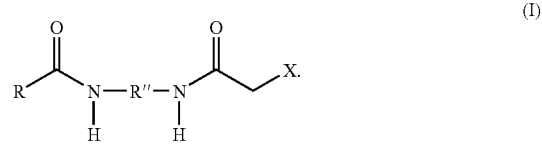

29 Claims, No Drawings

STARCH DERIVATIVES, STARCH ACTIVE SUBSTANCE CONJUGATES, METHOD FOR THE PRODUCTION THEREOF AND THEIR USE AS MEDICAMENTS

RELATED APPLICATIONS

This application is the U.S. National Stage of International Application No. PCT/EP03/01716, filed Feb. 20, 2003, and published in German, which claims the benefit of German Application No. 102 07 072.5, filed Feb. 20, 2002.

The present invention relates to starch derivatives, conjugates of such starch derivatives with active substances and a method for their preparation. The invention further relates to the use of starch/active-substance conjugates as drugs.

The conjugation of pharmaceutical active substances such as therapeutic proteins, antibiotics, nucleic acids, cytokines and hormones with polyethylene glycol derivatives ("pegylation") is a widely used method (Francis G. E. et al., Polyethylene glycol modification in tumour targeting and cytokine therapy, J. Drug Targeting (1995), 3: 321-340). Active substances that are in themselves water-insoluble, for example, are thus converted into soluble derivatives, which can then be administered into the blood stream.

Furthermore, it is possible to the molecular weight of active substances by the coupling of polyethylene glycol derivatives in such a way that filtration via the kidneys is no longer possible, i.e. that the so-called kidney barrier is overcome and the half-life periods of such derivatives is thus lengthened considerably compared with the unconjugated active substances. Moreover, as a result of the coupling with polyethylene glycol derivatives, it is possible to reduce the antigenicity of, for example, proteins of non-human origin, which would otherwise lead to immunological side-effects when administered.

Polyethylene glycol (PEG) has the drawback, however, that it is a non-metabolisable molecule and proteins derivatised therewith can lead to vacuolisation of the kidneys. It is therefore of particular interest to carry out derivatisations of active substances with metabolisable polymers, whose decomposition in the body can preferably be controlled. A suitable molecule for this is hydroxyethyl starch (HES), which has long been widely used as a plasma expander in various molecular specifications (DE 196 28 705 A1).

Even when administered in very high doses, HES exhibits side-effects only rarely and to a very small extent compared to with other plasma expanders, such as for example gelatin derivatives or dextranes, or also human albumin.

A further unsolved problem with the derivatisation of active substances, however, is the selective binding of the active substance to the carrier. In the case of proteins, it is for example desirable to carry out the coupling to a carrier at a sufficient distance from the reactive centre or from the receptor. Otherwise, the activity may be reduced or destroyed.

DE 196 28 705 A1 describes a method for binding haemoglobin to hydroxyethyl starch. However, the binding takes place relatively unselectively via the numerous free amino groups of the haemoglobin.

In view of the discussed prior art, the problem underlying the invention was to make starch derivatives available that bind as selectively as possible to an active substance.

Furthermore, such a starch derivative should be constituted so that as quantitative a binding as possible of an active substance takes place by covalent binding to this starch derivative.

The problem underlying the invention was also to make starch derivatives available whose decomposition behaviour can be controlled in the organism. In particular, the starch derivatives should be constituted such that they cannot pass the kidney barrier and a rapid secretion is prevented. As a result, the starch derivatives should exhibit an extended half-life period in the blood serum. However, the starch derivatives should be decomposable without residue within a physiologically reasonable period.

The solubility behaviour of active substances in aqueous phase and in organic solvents should also be able to be controlled within a wide range by their binding to the known starch derivatives.

Finally, the problem underlying the invention was to make available a method that is as simple and cost-effective as possible for the preparation of such starch derivatives and their coupling products with active substances.

These problems, as well as others which, though not mentioned literally, can however be deduced as self-evident from the correlations discussed herein or necessarily emerge therefrom, are solved with the starch derivatives described in claim 1. Expedient modifications of these starch derivatives according to the are protected in sub-claims 2-9 related back to claim 1. The conjugates of such starch derivatives with active substances are protected in claims 10-25.

With regard to a method for the preparation of starch/active substance conjugates with which the stated starch derivatives are obtained as an intermediate product, claims 26-28 provide a solution to the underlying problem.

Claims 29-31 describe drugs which include the starch/active-substance conjugates according to the invention and preferred medical applications of these drugs.

Through the preparation of compounds of the formula (I)

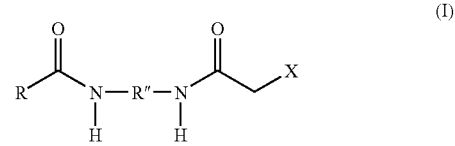

whereby X denotes a bromine or iodatome, R" denotes a straight-chained or branched alkyl, aryl or aralkyl compound R—CO— denotes an oxidised substituted or unsubstituted starch radical, which is oxidised at the reducing end group to form a carboxylic acid, it is possible to make starch derivatives available that bind extremely selectively to the SH functions of active substances.

The following advantages are also obtained with the compound according to the invention:

The special formulation of the starch derivatives prevents the latter from being able to pass the kidney barrier, as a result of which the half-life period of the active substance in the blood serum is extended. The half-life period describes the time after which half of the active substance used has been decomposed or secreted.

The compounds of formula (I) are decomposable without residue within a physiologically reasonable period, but on the other hand exhibit a controllable elimination behaviour.

Derivatives according to claim 1 can generally be prepared from any starch that has a group oxidisable into a carboxylic acid. Preferably, it is the reducing end group of a starch. It has been found that the aforementioned properties of the compound (I) can be particularly readily achieved when the oxidised starch radical R—CO— is a hydroxyethyl starch radical.

Starting products for obtaining hydroxyethyl starch are starches which have a high content of amylopectin, the highly branched component of starch, in particular potato starch, wax-maize starch, sorghum starch or wax-like rice starch.

These starches are subjected to a hydrolytic decomposition reaction for the rough pre-adjustment of the intended molecular weight. The molecular weight is reduced from approx. 20,000,000 Dalton to several million Dalton.

In the subsequent alkaline hydroxyethylation with known hydroxyethylation agents, the introduction of a hydroxyethyl group into position 2, 3 and 6 of the anhydroglucose unit is possible. Disubstituted units, such as 2,3-dihydroxyethylene hydroglucose, 2,6-dihydroxyethylene hydroglucose, are formed with less likelihood in the synthesis.

Two differently defined substitution degrees exist to cover the substitution by hydroxyethyl groups.

The substitution degree MS (molar substitution) is defined as the average number of hydroxyethyl groups per anhydroglucose unit. It is determined from the total number of hydroxyethyl groups in a sample, for example according to Morgan, by ether separation and subsequent quantitative determination of ethyliodide and ethylene, which are thereby formed.

On the other hand, the substitution degree DS (degree of substitution) is defined as the proportion of substituted anhydroglucose units of all anhydroglucose units. It can be determined from the measured quantity of unsubstituted glucose after hydrolysis of a sample. It emerges from these definitions that MS>DS. In the case where monosubstitution is present, i.e. each substituted anhydroglucose unit carries only one hydroxyethyl group, MS=DS.

A hydroxyethyl starch radical within the formula (I) of the present invention preferably has a substitution degree MS of 0.1 to 0.8. Particularly preferably, the hydroxyethyl starch radical has a substitution degree MS of 0.4 to 0.7.

The reactivity of the individual hydroxyethyl groups in the unsubstituted anhydroglucose unit with respect to hydroxyethylation is different depending on the reaction conditions. Within certain limits, the substitution sample, i.e. the individual, differently substituted anhydroglucoses which are statistically distributed over the individual polymer molecules, can be influenced by this. To advantage, the $C_2$- and the $C_5$-position are predominantly hydoxyethylated, whereby the $C_6$-position is substituted more frequently on account of its easier accessibility.

Within the scope of this invention, used is preferably made of hydroxyethyl starches (HES) substituted predominantly in the $C_2$ position, which are substituted as homogeneously as possible. The preparation of such HES is described in EP 0 402724 B2. They are decomposable without residue within a physiologically reasonable period, but on the other hand exhibit a controllable elimination behaviour. The predominant $C_2$ substitution makes the hydroxyethyl starch relatively difficultly decomposable for α-amylase. It is advantageous, if possible, for no anhydroglucose units substituted one after the other inside the polymer molecule to occur, in order to guarantee decomposability without residue. Furthermore, despite the low substitution, such hydroxyethyl starches possess a sufficiently high solubility in aqueous medium, so that the solutions are stable even over lengthier periods and no agglomerates or gels are formed.

Relaxed to the hydroxyethyl groups of the anhydroglucose units, a hydroxyethyl starch radical within the formula (I) of the present invention preferably has a ratio of $C_2$:$C_6$ substitution in the range from 2 to 12. Particularly preferably, the ratio of $C_2$:$C_6$ substitution amounts 3 to 11.

For the coupling with an active substance, hydroxyethyl starches (HES) are oxidised preferably at their reducing end into carboxylic acid or lactone. DE 196 28 705 A1 describes a method in which HES is oxidised with iodine/potassium hydroxide at the reducing end. Subsequent coupling to an active substance can take place via the acid function obtained.

The radical R—CO— in the compound of formula (I) according to the invention denotes in the preferred formula on an oxidised hydroxyethyl starch radical, which is oxidised at the reducing end group in the manner described to form a carboxylic acid.

Due to the use of the natural starting raw material amylopectin and also due to the method of preparation, in which separation of the polymer chains is necessary to a certain extent, hydroxyethyl starch is not present as a molecular-uniform substance a defined molecular weight, but as a mixture of molecules of differing size, which are also substituted variously by hydroxyethyl groups. The characterisation of such mixtures requires the use of statistically averaged magnitudes (see K. Sommermeyer et al., "Klinisch verwendete Hydroxyethylstärke: Physikalisch-chemische Charakterisierung" 271 (1987)). In order to denote the average molecular weight, therefore, the averaged molecular weight Mw is used. The general definition of this average value reads as follows:

$$M_w = \frac{\sum_i N_i \bullet M_i^w}{\sum_i N_i \bullet M_i^{w-1}}$$

A hydroxyethyl starch radical R—CO— within the formula (I) of the present invention preferably has an average molecular weight Mw of 2000 to 1,000,000 D (determined with gel permeation chromatography). Still more preferably, the average molecular weight Mw amounts to 5,000 to 500,000 D and most preferably to 8,000 to 250,000 D.

The group R" in the compound (I) can contain both saturated as well as unsated bonds. An alkyl, aryl or aralkyl radical as R" can also contain further substituents, such as for example alkyl, aryl, aralkyl, halogen, carbonyl, acyl, carboxyl, carboxylester, hydroxy, thiol, alkoxy and/or alkylthio substituents. In a preferred form of embodiment, R" is a group of the formula $(CH_2)_n$, whereby n denotes a whole number from 1 to 10. Particularly preferably, R" is an ethylene, propylene, butylene, pentamethylene, hexamethylene or octamethylene group.

The invention also relates to starch/active-substance conjugates of the general formula (II)

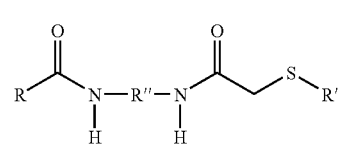

whereby R" denotes a straight-chained or branched alkyl, aryl or aralkyl group, R—CO— denotes an oxidised substituted or unsubstituted starch radical, which is oxidised at the reducing end group to form carboxylic acid, and R' is the radical of an active substance.

The starch/active-substance conjugates of formula (II) are coupling products from the previously described compounds of the formula (I) and an active substance, which contains at least one SH group. The radicals R—CO— and R" have the same significance as already explained previously with the aid of formula (I).

Preferred active substances R'—SH, which are contained as the radical R'—S— in the compounds of the formula (II), are selected from a peptide, a protein, an antibiotic, a nucleic acid, or a hormone. The prerequisite is that these compounds contain at least one SH group.

It can also be a protein or peptide to which a cysteine radical has been introduced by targeted mutagenesis. Inasmuch as no SH groups are present in proteins or peptides, it is possible within the scope of the present invention to use so-called cysteine-muteines of therapeutic proteins, with which an exchange or an introduction of cysteine radicals has been be carried out selectively by targeted mutagenesis using genetic engineering. Such an exchange is known among experts and is described, amongst others, in: A. Bendele et al., Short Communication: Renal Tubular Vacuolation in Animals Treated with Polyethylene-Glycol conjugated Proteins, Toxicological Sciences 42, 152-157 (1998).

SH functions can also be introduced into active substances carrying a primary amino group by conversion with 2-iminothiolane (Trauts reagent), before the active substances are reacted with compounds of the formula (I). The introduction of SH functions by this method into active substances, such as for example into proteins, is generally known amongst experts.

Therapeutic antibodies, antibody fab fragments and antibody F(ab')₂ fragments are preferred active-substance proteins. On account of their relatively low molecular weight, such antibody fragments are easily passable through the kidneys and can be extended in their serum half-life period by derivatisation with starch. It has also been established within the scope of the present invention that the hydrolytic decomposition of the antibodies or antibody fragments by proteases can be reduced with the aid of derivatisation with hydroxyethyl starch.

In further preferred forms of embodiment, the active substance is a cytokine, in particular an interferon α 2a or an interferon α 2b, or erytropoetin.

Within the scope of the present invention, it has been established that the solubility of an active substance in aqueous medium can be influenced when the latter is coupled to a compound of the formula (I) and converted into a starch/active-substance conjugate of the formula (II).

Within the scope of the invention, it has also been established that the solubility of a protein or enzyme in organic solvents can be increased when the protein or enzyme is coupled to a compound of the formula (I) and converted into a starch/active-substance conjugate of the formula (II). Dimethyl formamide, dimethyl sulphoxide or dimethyl acetamide are preferred aprotic solvents.

The present invention also relates in a further aspect to a method for the preparation of the previously describe starch/active-substance conjugates of the formula (II). The initially described starch derivative of the formula (I) is obtained as an intermediate product of this method. The method is characterised by the following steps:

a) The reducing end groups of a substituted or unsubstituted starch are first selectively oxidised to form the carboxyl or lactone group. Hydroxyethyl starch is preferably used.

The oxidation can take place for example with iodine/potassium hydroxide according to DE 196 28 705 A1.

b) The oxidised starch or hydroxyethyl starch obtained in step a) is reacted at its carboxylic group or lactone group with a diamine.

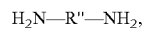

whereby R" denotes an alkyl, aryl or aralkyl radical, which can be branched or unbranched. The stated radicals can also contain saturated as well as unsaturated bonds. An alkyl radical, aryl radical or aralkyl radical can also contain further substituents, such as for example alkyl, aryl, aralkyl, halogen, carbonyl, acyl, carboxyl, carboxyl, carboxylester, hydroxy, thiol, alkoxy and/or alkylthio substituents.

Preferably, R" is an unbranched saturated alkyl radical $(CH_2)_n$, whereby n denotes a whole number from 2 to 10. Particularly preferred compounds are ethylene diamine, 1,3-diaminopropane, 1,4-diaminobutane, 1,5-diaminopentane, 1,6-daminohexane and 1,8-diaminooctane.

By reacting the oxidised substituted or unsubstituted starch with the diamine described above, a compound of the formula (III)

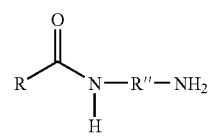

is obtained, in which R—CO— represents an oxidised substituted or unsubstituted starch radical, as already described at the outset with the aid of the formula (I), said starch radical being oxidised at the reducing end group to form a carboxylic acid.

c) The compound of the formula (III) is reacted with a halogen acetic and 1-ethyl-3-(3-dimethylaminopropyl) carbodiimide as an activator to form a compound of the formula (I)

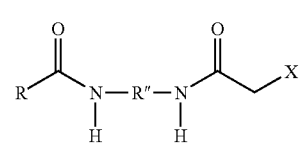

in which X denotes a bromine or iodatome.

d) Finally, the compound of the formula (I) is reacted with an active substance with at least one thiol radical R'—SH to form a starch/active-substance conjugate of the general formula (II)

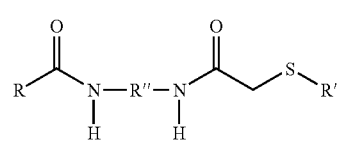

whereby R' represents an active-substance radical.

It has been found that, under neutral to slightly alkaline conditions, the thiol group of an active substance reacts more rapidly than other reactive groups with compounds of the formula (I). Preferably, the pH value amounts to 6.5-8.5. Under these conditions, deprotonisation of the thiol group takes place to thiolation, which is particularly reactive and reacts selectively with compounds of the formula (I).

It has been established that the derivatisation of an active substance by coupling to a starch can be carried out extremely selectively with the method described above. Selective means in this case that an active substance essentially reacts solely via its thiol groups with compounds of the formula (I) and that the coupling to the starch/active-substance conjugate essentially takes place solely via thiol ether bonds.

Particularly preferably, the coupling method is carried out with peptides or proteins containing SH groups. A reaction of the compound (I) is also possible with SS groups of a protein or peptide, after the latter have been converted into SH groups.

The yields of the reaction of compounds of the formula (I) with a peptide or protein containing SH groups amounts, depending on the molecular weight of the protein or peptide and the number of SH or SS groups, to between 20% and 90%. In the favourable case, therefore, a largely quantitative coupling of an active substance to the starch carrier can be achieved.

It is also possible to react an intermediate product of the formula (III) in step c) of the method described above with other commonly used cross-inking agents instead of with a halogen acetic acid. In this case, a functional group of the cross-linking agent reacts with the primary amino group of the compound (III). In the following step, one of the remaining functional groups of the cross-linking agent reacts with a functional group of an active substance, preferably with an SH group, as a result of which a starch/active-substance conjugate is formed. Commonly used cross-linking agents are, for example, bifunctional cross-linking agents with α-ω-terminal identical or different functional groups. An overview of such cross-linking agents can be found in the catalogue from the in Perbio (2001/2002).

Furthermore, it is possible, and self-evident to the expert, to react a starch radical or hydroxyethyl starch radical described at the outset, which is oxidised at the reducing end group to form a carboxylic acid, directly with one of the commonly used cross-linking agents described above. In this case, a functional group of the cross-linking agent reacts with the carboxyl group of the oxidised starch or hydroxyethyl starch. In the following step, one of the remaining functional groups of the cross-lining agent reacts with a functional group of an active substance, preferably with an SH group, as a result of which a starch/active-substance conjugate is formed According to one aspect of the present invention, the starch derivatives of active substances described above are used for the preparation of a drug. Preferably, it is a drug for the treatment of infectious diseases or hormonal disturbances. In this connection, such a drug can contain standard pharmaceutical accessory agents.

The invention is described below with an ample, although the invention is not intended to be restricted thereto.

EXAMPLE 1

10 g of conjugate of oxidised hydroxyethyl starch with a mean molecular weight Mw of 40,000 and a substitution degree MS of 0.2, prepared analogous to DE 196 28 705 A1, was dissolved together with ethylene diamine in 50 ml of distilled water. 0.2 g of bromoacetic acid was dissolved in 5 ml of distilled water, the pH value was set at 4.5 with 0.01 normal soda lye and this solution was added to the amino-functionalised hydroxyethyl starch described above. Whilst stirring, 0.1 g of 1-ethyl-3-(3-dimethylaminopropyl)carbodiimide was added to the reaction mixture, and the pH value was held for an hour at 4.5 by adding 0.01 normal hydrochloric acid and then 0.01 normal so lye. After a further 2 hours reaction time, the reaction product was ultra-filtered and then precipitated with ethanol and washed and dried with light protection in a vacuum.

The invention claimed is:

1. A starch derivative comprising formula (I):

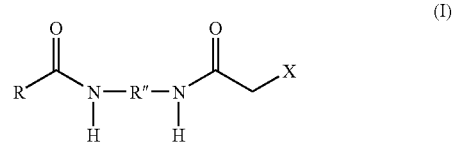

wherein
X is a bromine or iodatome;
R" is a straight-chained or branched alkyl, aryl, or aralkyl group; and
R—CO— is an oxidized substituted or unsubstituted starch radical, which is oxidized at the reducing end group to form a carboxylic acid.

2. The starch derivative of claim 1, wherein R" is a group of the formula $(CH_2)_n$ and n denotes a whole number from 1 to 10.

3. The starch derivative of claim 1, wherein the radical R—CO— is a hydroxyethyl starch radical oxidized to form carboxylic acid, said hydroxyethyl starch radical having an average molecular weight of from 2,000 to 1,000,000 Daltons.

4. The starch derivative of claim 3, wherein said hydroxyethyl starch radical has an average molecular weight of from 5,000 to 500,000 Daltons.

5. The starch derivative of claim 4, wherein said hydroxyethyl starch radical has an average molecular weight of from 8,000 to 250,000 Daltons.

6. The starch derivative of claim 1, wherein the radical R—CO— is a hydroxyethyl starch radical oxidized to form carboxylic acid, said hydroxyethyl starch radical having a substitution degree MS of from 0.1 to 0.8.

7. The starch derivative of claim 6, wherein said hydroxyethyl starch radical has a substitution degree MS of from 0.4 to 0.7.

8. The starch derivative of claim 1, wherein the radical R—CO— is a hydroxyethyl starch radical oxidized to form carboxylic acid, said hydroxyethyl starch radical having a ratio of $C_2:C_6$ substitution in the range of from 2-12 related to the hydroxyethyl groups of the anhydroglucose units.

9. The starch derivative of claim 8, wherein said hydroxyethyl starch radical has a ratio of $C_2:C_6$ substitution in the range of from 3-11 related to the hydroxyethyl groups of the anhydroglucose units.

10. A starch/active-substance conjugate comprising formula (II)

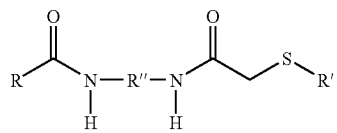

wherein
R" denotes a straight-chained or branched alkyl, aryl, or aralkyl group;
R—CO— denotes an oxidized substituted or unsubstituted starch radical, which is oxidized at the reducing end group to form a carboxylic acid; and
R' is the radical of an active substance.

11. The starch/active-substance conjugate of claim 10, wherein R" is a group of the formula $(CH_2)_n$ and n denotes a whole number from 1 to 10.

12. The starch/active-substance conjugate of claim 10, wherein the radical R—CO— is a hydroxyethyl starch radical oxidized to form carboxylic acid, said hydroxyethyl starch radical having an average molecular weight of from 2,000 to 1,000,000 Daltons.

13. The starch/active-substance conjugate of claim 12, wherein said hydroxyethyl starch radical has an average molecular weight of from 5,000 to 500,000 Daltons.

14. The starch/active-substance conjugate of claim 13, wherein said hydroxyethyl starch radical has an average molecular weight of from 8,000 to 250,000 Daltons.

15. The starch/active-substance conjugate of claim 10, wherein the radical R—CO— is a hydroxyethyl starch radical oxidized to form carboxylic acid, said hydroxyethyl starch radical having a substitution degree MS of from 0.1 to 0.8.

16. The starch/active-substance conjugate of claim 15, wherein said hydroxyethyl starch radical has a substitution degree MS of from 0.4 to 0.7.

17. The starch/active-substance conjugate of claim 10, wherein the radical R—CO— is a hydroxyethyl starch radical oxidized to form carboxylic acid, said hydroxyethyl starch radical having a ratio of $C_2:C_6$ substitution in the range of from 2-12 related to the hydroxyethyl groups of the anhydroglucose units.

18. The starch/active-substance conjugate of claim 17, wherein said hydroxyethyl starch radical has a ratio of $C_2:C_6$ substitution in the range of from 3-11 related to the hydroxyethyl groups of the anhydroglucose units.

19. The starch/active-substance conjugate of claim 10, wherein the active substance is selected from a peptide, a protein, an antibiotic, a nucleic acid, or a hormone.

20. The starch/active-substance conjugate of claim 19, wherein the protein is an antibody, an antibody fab fragment, or an antibody $F(ab')_2$ fragment.

21. The starch/active-substance conjugate of claim 19, wherein the protein is an erythropoetin.

22. The starch/active-substance conjugate of claim 19, wherein the protein is a peptide or protein in which a cysteine radical has been inserted by targeted mutagenesis.

23. The starch/active-substance conjugate of claim 19, wherein it concerns an active substance in which an SH function has been inserted by reaction with 2-iminothiolane.

24. The starch/active-substance conjugate of claim 19, wherein the active substance is a cytokine.

25. The starch/active-substance conjugate of claim 24, wherein the cytokine is selected from interferon α 2a and interferon α 2b.

26. A method of preparing starch/active-substance conjugates, the method comprising the steps of:
a) oxidizing the reducing end groups of a substituted or unsubstituted starch to form a carboxyl or a lactone group;
b) reacting the carboxyl group or the lactone group prepared in step a) with a diamine H2N—R"—NH2 to form a compound of formula (III)

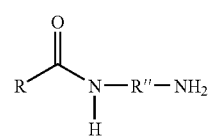

wherein
R" is a straight-chained or branched alkyl, aryl, or aralkyl group, and
R—CO— is an oxidized substituted or unsubstituted starch radical, which is oxidized at the reducing end group to form a carboxylic acid;
c) reacting the compound of formula (II) with a halogen acetic acid and 1-ethyl-3-(3-dimethylaminopropyl) carbodiimide as an activator to form a compound of formula (I):

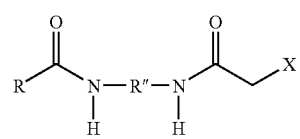

wherein X is a bromine or iodatome; and
d) reacting the compound of formula (I) with an active substance R'SH containing at least one SH group to form a starch/active-substance conjugate of general formula (II):

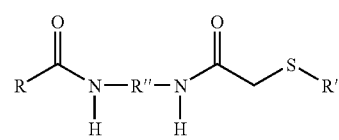

wherein R' is an active-substance radical.

27. The method of claim 26, wherein R" is a group of the formula $(CH_2)_n$ and n is a whole number from 1 to 10.

28. The method of claim 26, wherein the reaction of step d) is carried out at a pH value of between 6.5 and 8.5.

29. A pharmaceutical compound, comprising a carrier or diluent and a starch/active-substance conjugate of general formula (II)

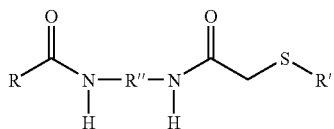
(II)
wherein
R" denotes a straight-chained or branched alkyl, aryl, or aralkyl group;
R—CO— denotes an oxidized substituted or unsubstituted starch radical, which is oxidized at the reducing end group to form a carboxylic acid; and
R' is the radical of an active substance.
* * * * *

UNITED STATES PATENT AND TRADEMARK OFFICE
CERTIFICATE OF CORRECTION

PATENT NO. : 7,285,661 B2  Page 1 of 1
APPLICATION NO. : 10/504892
DATED : October 23, 2007
INVENTOR(S) : Klaus Sommermeyer et al.

It is certified that error appears in the above-identified patent and that said Letters Patent is hereby corrected as shown below:

Column 10, claim 26, line 30, delete "(H)" and insert --(III)--

Signed and Sealed this

Twenty-seventh Day of May, 2008

JON W. DUDAS
*Director of the United States Patent and Trademark Office*